United States Patent
Gegnas

Patent Number: 6,030,996
Date of Patent: Feb. 29, 2000

[54] MUR D INHIBITING COMPOUNDS, COMPOSITIONS CONTAINING SUCH COMPOUNDS AND METHODS OF USE

[75] Inventor: Laura D. Gegnas, Monmouth Junction, N.J.

[73] Assignee: Merck & Co., Inc., Rahway, N.J.

[21] Appl. No.: 09/038,437

[22] Filed: Mar. 11, 1998

Related U.S. Application Data

[60] Provisional application No. 60/041,010, Mar. 27, 1997.

[51] Int. Cl.$^7$ .............................. H01N 43/16; C07F 9/28; C07D 315/06
[52] U.S. Cl. .......................... 514/459; 514/460; 549/216; 549/217; 549/218; 549/219; 549/417; 549/418-420
[58] Field of Search ................... 549/217, 417, 549/418, 420, 216, 218, 219; 514/459, 460

[56] References Cited

U.S. PATENT DOCUMENTS 4,650,862  3/1987  Imamura et al. ............... 536/17.1

OTHER PUBLICATIONS

T. D. Bugg and C. T. Walsh, *Natural Products Report;* pp. 199–215, (1992).

S. M. Berge et al., *J. Pharm. Sci,* 66(1), pp. 1–19 (1977).

E. K. Baylis et al, *J. Chem So. Perkins Trans.,* I, pp. 2845–2853 (1984).

*Primary Examiner*—John Kight
*Assistant Examiner*—Raymond Covington
*Attorney, Agent, or Firm*—James M. Hunter, Jr.; Richard C. Billups; Mark R. Daniel

[57] ABSTRACT

The present invention addresses compounds which inhibit Mur D. The compounds are represented by structural formula 1:

wherein:

X represents OH, $OC_{1-6}$ alkyl, O-aryl, O-Har, uridinyl, 5-iodouridinyl or $O—Y^+$, wherein $Y^+$ represents a charge balancing group; $R^1$ and $R^2$ independently represent H or $C_{1-6}$ alkyl, or $R^1$ and $R^2$ taken together represent $C_{1-6}$ alkylene unsubstituted or substituted with from 1–2 aryl or Har groups; W represents H, aryl, $C_{1-6}$ alkyl or a charge balancing group; each M independently represents a member selected from the group consisting of: H, a charge balancing group and a protecting group.

Salts and hydrates thereof are included.

Also included are pharmaceutical compositions and methods of treatment.

17 Claims, No Drawings

MUR D INHIBITING COMPOUNDS, COMPOSITIONS CONTAINING SUCH COMPOUNDS AND METHODS OF USE

This application claims benefit of provision application Ser. No. 60/041,010 filed Mar. 27, 1997.

BACKGROUND OF THE INVENTION

UDP-N-acetylmuramoyl-L-alanine:D-glutamate ligase (Mur D) is an enzyme which is involved in bacterial peptidoglycan biosynthesis. This enzyme is part of the Mur enzyme pathway.

Many antibiotics, such as penicillins, cephalosporins and vancomycin interfere with bacterial peptidoglycan biosynthesis. The target enzyme could thus be deemed critical for cell wall synthesis. This applies in both Gram positive and Gram negative microorganisms. See, e.g., Bugg, T. D., et al. *Natural Product Reports* (1992) 199–215.

The present invention addresses compounds which inhibit Mur D, compositions which contain such compounds and methods of use. The compounds disclosed herein therefore form an important contribution to antibiotic therapy. These and other advantages will be apparent from the disclosure contained herein.

SUMMARY OF THE INVENTION

A compound which is represented by structural formula 1 is disclosed:

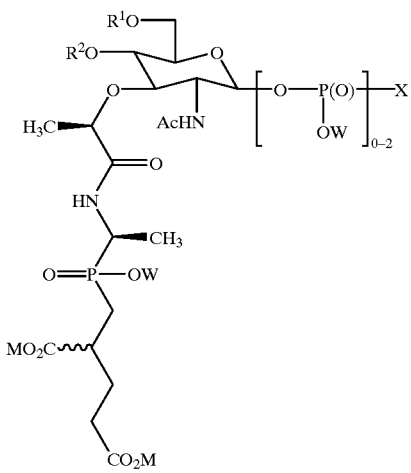

wherein:

X represents OH, $OC_{1-6}$ alkyl, O-aryl, O-Har, uridinyl, 5-iodouridinyl or $O-Y^+$, wherein $Y^+$ represents a charge balancing group;

$R^1$ and $R^2$ independently represent H or $C_{1-6}$ alkyl, or $R^1$ and $R^2$ taken together represent $C_{1-6}$ alkylene unsubstituted or substituted with from 1-2 aryl or Har groups;

W represents H, aryl, $C_{1-6}$ alkyl or a charge balancing group;

each M independently represents H, a charge balancing group or a protecting group.

Salts and hydrates thereof are included.

Also disclosed is a pharmaceutical composition which is comprised of a compound of formula 1 or a pharmaceutically acceptable salt or hydrate thereof in combination with a carrier.

Also disclosed is a method of treating a bacterial infection in a mammalian patient in need of such treatment which is comprised of administering to said patient a compound of formula I or a salt or hydrate thereof in an amount which is effective for treating a bacterial infection.

DETAILED DESCRIPTION OF THE INVENTION

The invention is described herein in connection with the following definitions unless otherwise specified.

The term "$C_{1-6}$ alkyl" means a monovalent alkyl group containing 1–6 carbon atoms, which may be straight, branched or cyclic as appropriate. Examples of alkyl groups include methyl, ethyl, propyl, isopropyl, n-butyl, t-butyl, cyclopentyl and cyclohexyl. Preferably $C_{1-6}$ alkyl represents a member selected from the group consisting of methyl, ethyl, n-propyl, n-butyl, t-butyl and cyclohexyl.

The term "$C_{1-6}$ allylene" refers to a divalent alkyl group.

When a variable represents a "charge balancing group" or a "charge balancing ion", this refers to a moiety that is present in association with an oppositely charged moiety. When the group is specified as a cation, the moiety is positively charged. The charged moiety may or may not be considered part of the compound of formula 1. Examples of charge balancing groups include positively charged ions, such as metal cations, e.g., bearing a positive charge +1 or +2, such as $Na^+$, $K^+$, $Mg^{2+}$, $Mn^+$, $Ca^{2+}$ and the like. These moieties provide overall charge neutrality, and thus would be present in an appropriate molar amount. Thus, for example, divalent cations would be in association with two negative charges, either from the same or different molecules of formula 1. Similarly when a divalent cation is present in association with a single negative charge, a half molar equivalent of the cation may be present.

The term "aryl" refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The terms "heteroaryl" and "Har" refer to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

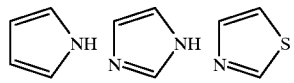

pyrrole (pyrrolyl) imidazole (imidazolyl) thiazole (thiazofyl)

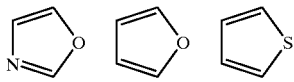

oxazole (oxazolyl) furan (furyl) thiophene (thienyl)

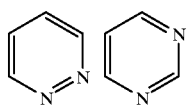

pyridazine (pyridazinyl) pyrimidine (pyrimidinyl)

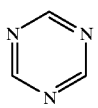

triazine (triazinyl)

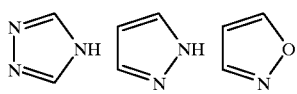

triazole (triazolyl) pyrazole (pyrazolyl) isoxazole (isoxazolyl)

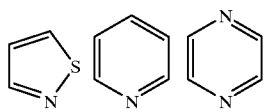

isothiazole (isothiazolyl) pyridine (pyridinyl) pyrazine (pyrazinyl)

Uridine and uridinyl are used interchangeably and refer to the following structures:

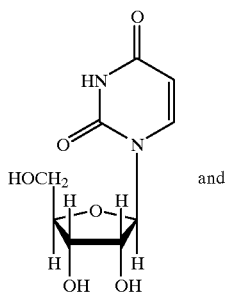

and

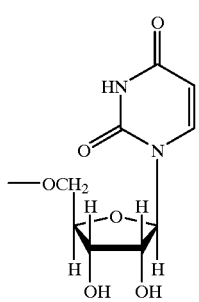

X represents OH, $OC_{1-6}$ alkyl, O-aryl, O-Har, uridinyl, 5-iodouridinyl or O—$Y^+$, wherein $Y^{30}$ represents a charge balancing group. Preferably X represents OH, O-aryl, O-Har, uridinyl, 5-iodouridinyl or O—$Y^+$, with $Y^{30}$ as defined above representing a charge balancing group.

$Y^+$ preferably represents a charge balancing group selected from the group consisting of: $Na^+$, $K^+$ and $Ca^{2+}$. Within this subset, all other variable groups are as originally defined.

$R^1$ and $R^2$ independently represent H or $C_{1-6}$ alkyl, or $R^1$ and $R^2$ taken together represent $C_{1-6}$ alkylene, $C_{1-6}$ alkylene substituted with from 1–2 aryl or Har groups. Preferably $R^1$ and $R^2$ independently represent H or $C_{1-6}$ alkyl, and more preferably each represents H or methyl. Within this subset, all other variable groups are as originally defined.

W represents H, aryl, $C_{1-6}$ alkyl or a charge balancing group. Preferably W represents H, $C_{1-6}$ alkyl or a charge balancing group, and most preferably W represents H or a charge balancing group selected from the group consisting of: $Na^+$, $K^+$ and $Ca^{2+}$ (half molar equivalent). Within these subsets, all other variable groups are as originally defined.

From 0 to 2 phosphate groups are linked through the 2-aminoglycoside ring at position 1. Preferably 1–2 phosphates (a phosphate or a diphosphate) are present at this position. More preferably one phosphate group is present at this position.

Each M independently represents a member selected from the group consisting of: H, a charge balancing group and a protecting group. Preferably each M represents H or a charge balancing group selected from the group consisting of: $Na^+$, $K^+$ and $Ca^{2+}$ (half molar equivalent).

A subset of compounds which is of particular interest is defined in accordance with compound 1-a:

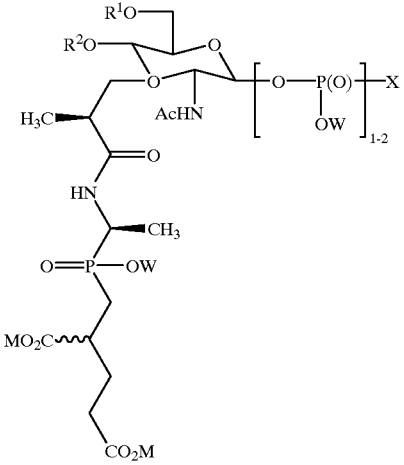

1-a wherein:

X represents OH, O-aryl, O-Har, uridinyl, 5-iodouridinyl or O—$Y^+$, wherein $Y^{30}$ represents a charge balancing group selected from the group consisting of: $Na^+$, $K^+$ and $Ca^{2+}$ (half molar equivalent);

$R^1$ and $R^2$ independently represent H or $C_{1-6}$ alkyl, or $R^1$ and $R^2$ taken together represent $C_{1-6}$ alkylene substituted with from 1–2 aryl groups;

W represents H or a charge balancing group selected from the group consisting of: $Na^+$, $K^+$ and $Ca^{2+}$ (half molar equivalent);

and each M independently represents H or a charge balancing group selected from the group consisting of: $Na^+$, $K^+$ and $Ca^{2+}$ (half molar equivalent).

Salts and hydrates thereof are included.

Examples of suitable protecting groups include: $C_{1-6}$ alkyl, benzhydryl, o-nitrobenzyl, p-nitrobenzyl (PNB), 2-naphthylmethyl, allyl, 2-chloroallyl, benzyl (Bn), 2,2,2- trichloroethyl, trimethylsilyl (TMS), t-butyldimethylsilyl (TBDMS), t-butyldiphenylsilyl, 2-(trimethylsilyl)ethyl, phenacyl, p-methoxybenzyl, acetonyl, p-methoxyphenyl, 4-pyridylmethyl and t-butyl. Preferred protecting groups include $C_{1-6}$ alkyl, benzhydryl, PNB, allyl, Bn, TMS, TBDMS, acetonyl and p-methoxyphenyl. More preferred are $C_{1-6}$ alkyl, particularly methyl, isopropyl, t-butyl and cyclohexyl, TMS, PNB and allyl.

Many other suitable protecting groups are known in the art. See, e.g., T. W. Greene, *Protective Groups in Organic Synthesis,* John Wiley & Sons, Inc., 1981 (Chapters 2 and 5).

Preferred compounds falling within the scope of the present invention include the following:

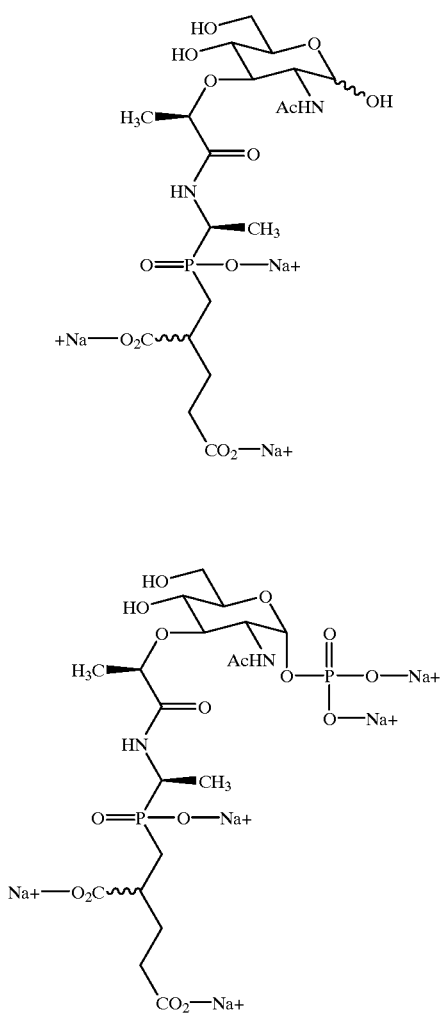

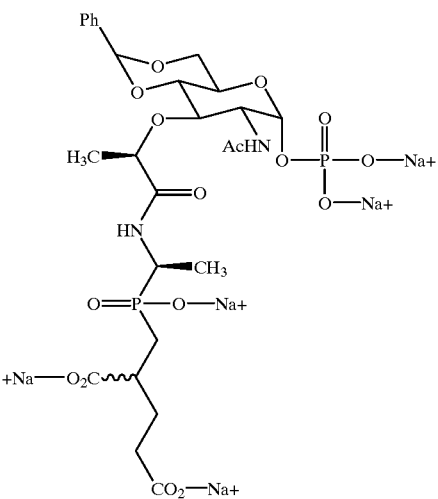

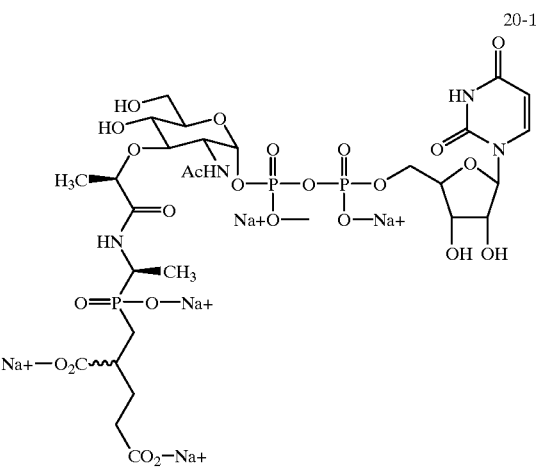

Other salts, including pharmaceutically acceptable salts and hydrates are included as well.

Preferred intermediates which are useful in making compounds of the present invention include the following:

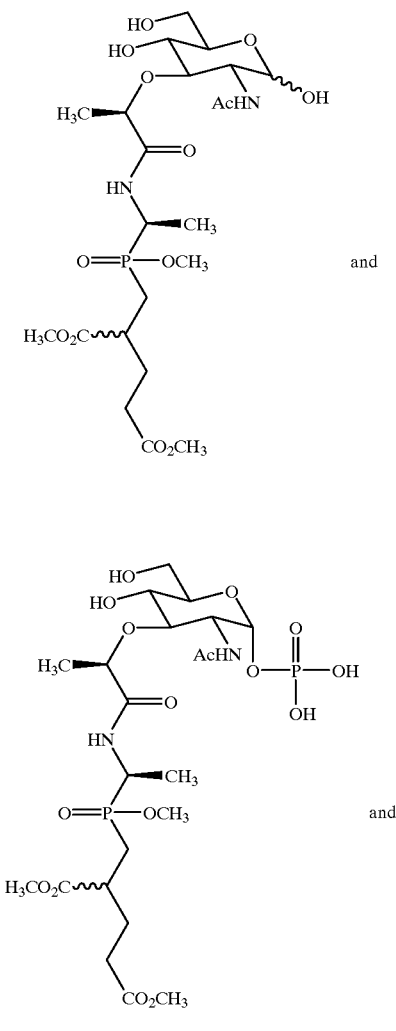
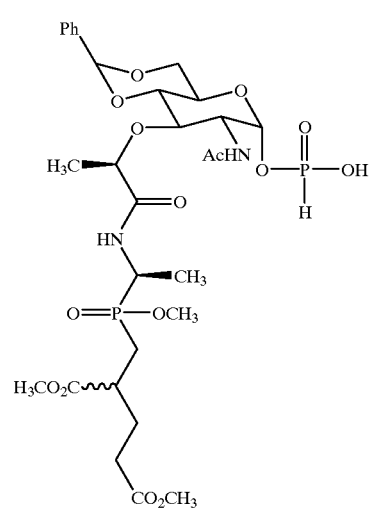
and
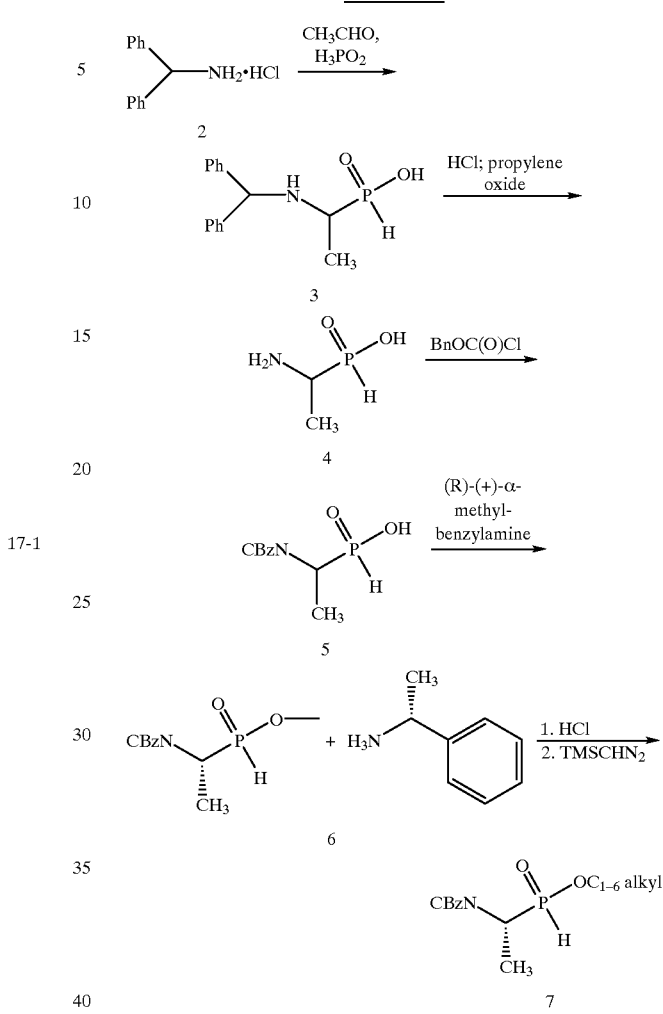
Ph=phenyl
Bn=benzyl
Ac=Acetyl
CBz =benzyloxycarbonyl
T-Alk-SCHN$_2$=trimethylsilyidiazomethane
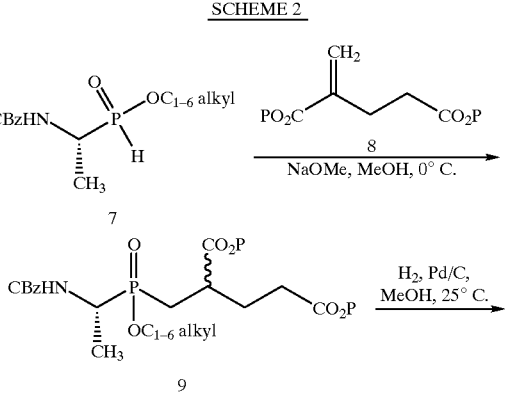
The compounds of the invention can be obtained in accordance with the following general synthesis schemes.

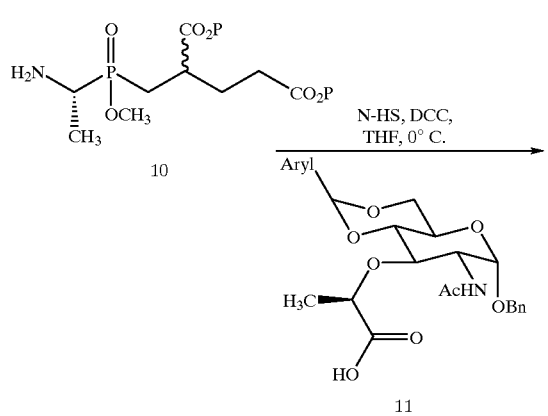
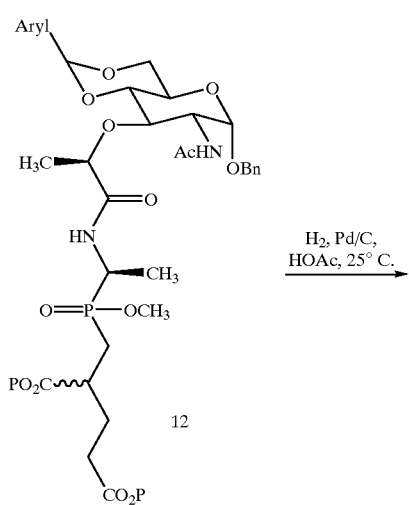
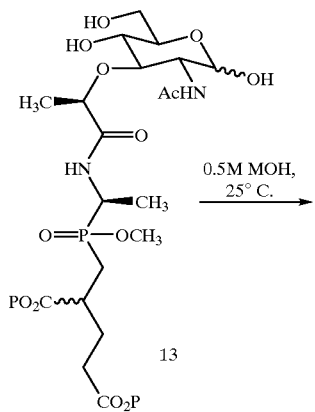
N—HS = N-hydroxysuccinimide   DCC = dicyclohexylcarbodiimide
P = Protecting group
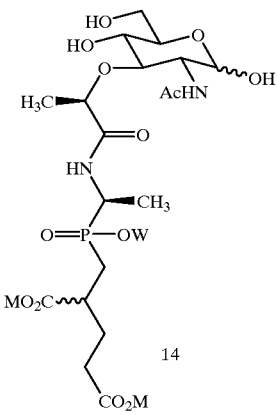
M, W = charge balancing groups
SCHEME 3
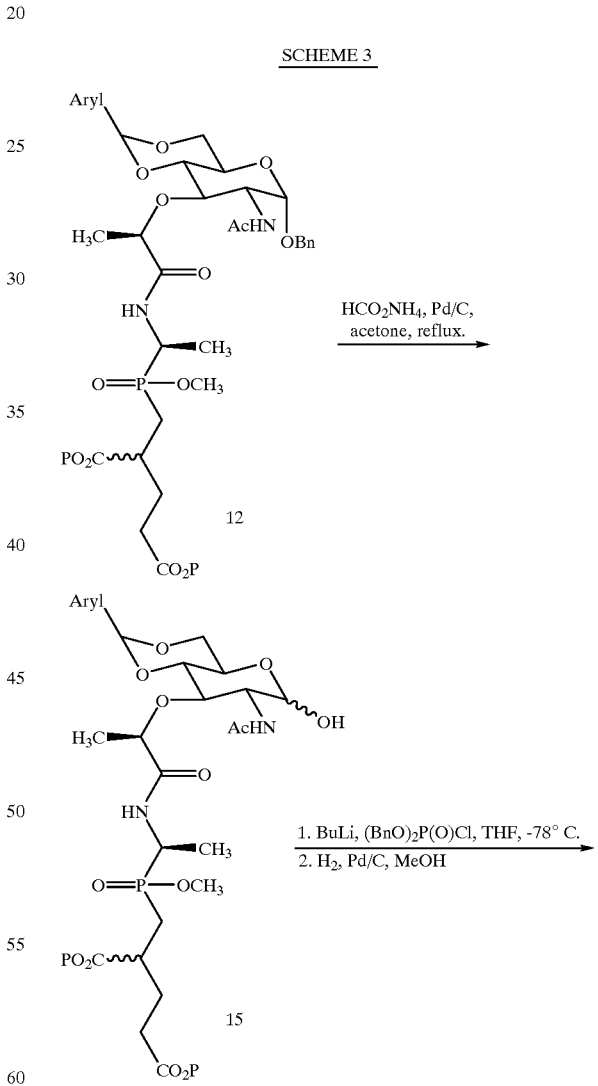

-continued
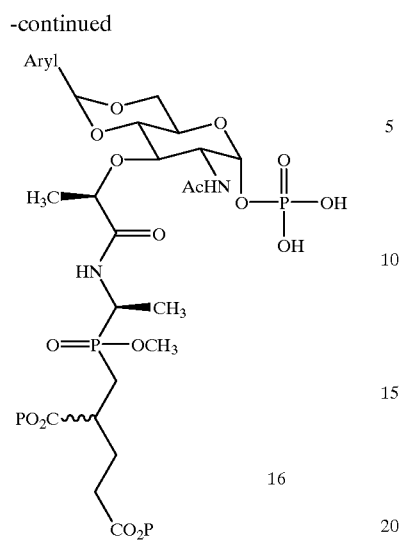
SCHEME 4
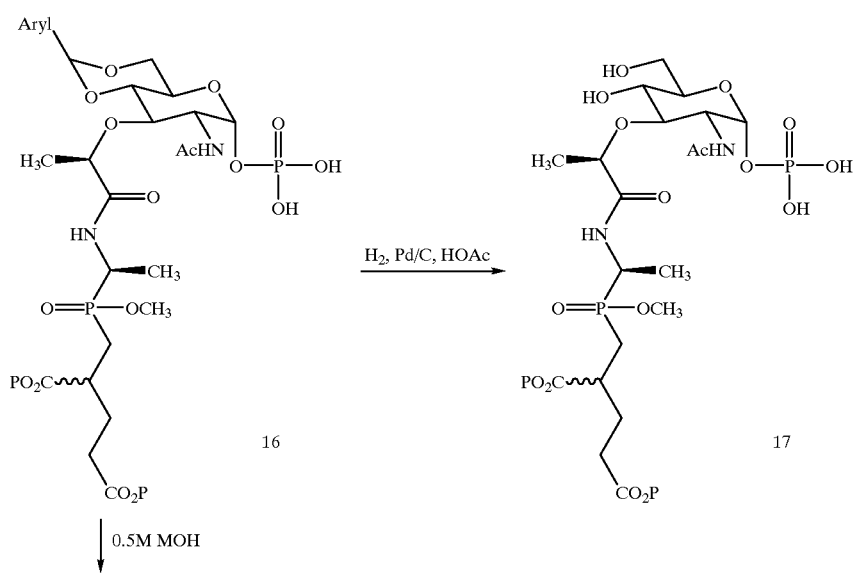

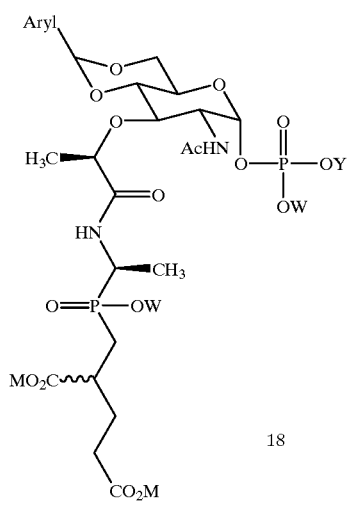

Y, M, W = charge balancing groups

SCHEME 5

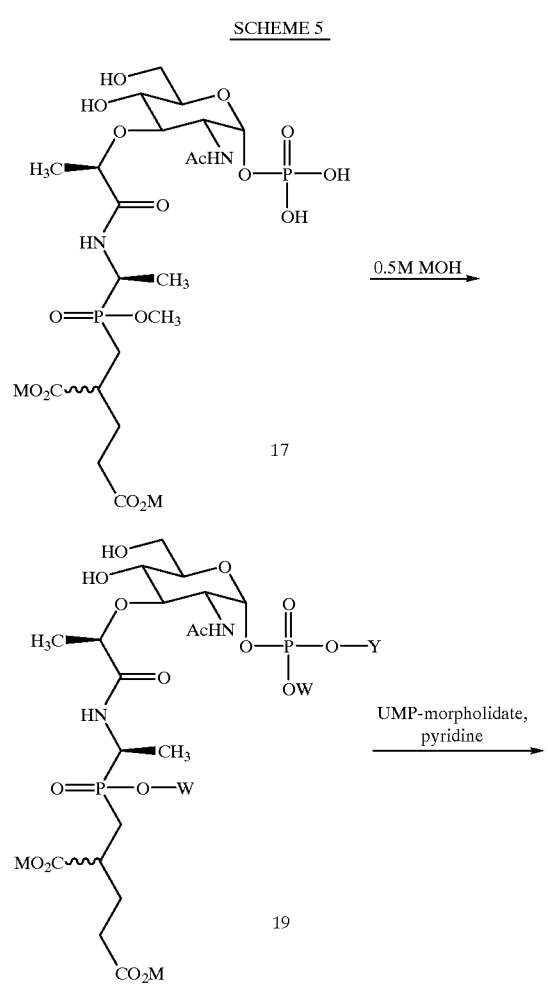

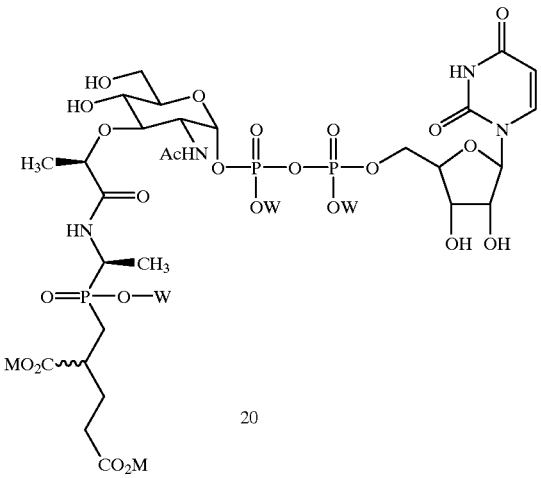

Methyl [1-[(benzyloxycarbonyl)amino]ethyl]phosphinate (7) with an absolute configuration corresponding to that of L-alanine is assembled using the procedure of Baylis, et al. J. Chem. Soc. Perkin Trans. I 1984, 2845–2853 and Parsons, W. H. et al. J. Med. Chem. 1988, 31, 1772–1778. Condensation of amino diphenylmethane hydrochloride (2) with acetaldehyde in the presence of hypophosphorous acid followed by acid-mediated deprotection of the amine affords racemic 1-aminoethyl phosphonous acid (4). The N-benzyloxycarbonyl derivative (5) is resolved by recrystallization of the salt with (R)-(+)-α-methylbenzylamine (6) to constant optical rotation. Treatment of the salt with HCl liberates (−)-1 -benzyloxycarbonylaminoethyl phosphonous acid. Esterification is accomplished with trimethylsilyldiazomethane.

The methyl phosphinate is then treated with sodium methoxide and di-protected 2-methylene pentanedioate to give the entire dipeptide segment (9).

The protecting group is removed via hydrogenolysis and the amine (10) is allowed to react with benzyl-N-acetyl-4, 6-O-benzylidene muramic acid (11) which is activated with N-hydroxysuccinimide/DCC to afford the amide 12. Removal of the protecting groups by hydrogenolysis in acetic acid followed by saponification of the resulting triol (13) affords the appropriate salt (14).

To phosphorylate the anomeric position, the benzyl group in 12 is selectively removed by catalytic transfer hydrogenation to afford the anomeric hydroxy compound 15. Deprotonation with n-BuLi followed by phosphorylation with dibenzylchlorophosphate gives the dibenzyl glycosyl phosphate ester which is hydrogenolyzed in the presence of Pd/C to afford the anomeric phosphate 16. Saponification of triester 16 affords the pentasodium salt 18.

Alternatively, the benzylidene group is removed via hydrogenation in the presence of Pd/C and acetic acid to give a diol 17. Saponification of 17 gives the salt 19 which is converted to 20 by coupling with uridine 5'-monophospho-morpholidate in pyridine.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is concerned with pharmaceutical compositions and various methods which utilize a compound of formula I.

Salt forms which are not pharmaceutically acceptable are included in the present invention, and can be converted to those salts which are pharmaceutically acceptable.

The pharmaceutically acceptable salt forms of the compound of formula 1 mentioned above include the various possibilities for charge balancing moieties.

Numerous salt-forming ions are recited in Berge, S. M., et al. J. Pharm. Sci. 66(1): 1–16 (1977), the teachings of which are incorporated herein by reference.

A preferred group of salt-forming cations is selected from the group consisting of: sodium, potassium, calcium, and magnesium.

More preferably the salt-forming cation is selected from the group consisting of: $Na^+$, $Ca^{+2}$ and $K^+$.

The compounds of the present invention are inhibitors of MurD and therefore have application as antibacterial agents. In one aspect, the compounds are active against various gram-positive and to a lesser extent gram-negative bacteria, and accordingly find utility in human and veterinary medicine. In another aspect, the compounds are useful in screening for the presence of other compounds which are inhibitors of Mur D or of other enzymes in the Mur pathway.

The compound of the invention may be used in a variety of pharmaceutical preparations. Compositions for injection, the preferred route of delivery, may be prepared in unit dosage form in ampoules or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the active ingredient may be in the form of a powder, which can be reconstituted with a suitable carrier such as sterile water, normal saline and the like at the time of administration. The powder can be in lyophillized or non-lyophillized form.

Oral compositions are typically in the form of tablets, capsules, solutions or suspensions. Such compositions may likewise be packaged in unit dose or multidose containers. In these oral compositions, the pharmaceutically acceptable carriers may be comprised of diluents, tabletting and granulating aids, lubricants, disintegrants, buffers, sweeteners, preservatives and the like.

Topical applications may be formulated with a pharmaceutically acceptable carrier in the form of hydrophobic or hydrophilic ointments, creams, lotions, solutions, paints or powders.

The dosage to be administered depends to a large extent upon the condition and size of the subject being treated as well as the route and frequency of administration. The parenteral route (by injection) is preferred for generalized infections. Such matters, however, are typically left to the discretion of the clinician according to principles of treatment well known in the antibacterial arts.

Compositions for human delivery per unit dosage, whether liquid or solid, may contain from about 0.01% to about 99% of active material, the preferred range being from about 10–60%. The composition will generally contain from about 15 mg to about 2000 mg of the active ingredient; however, in general, it is preferable to employ a dosage amount in the range of from about 250 mg to 1000 mg. In parenteral administration, the unit dosage is usually the compound I in a sterile water or saline solution or in the form of a soluble powder intended for solution.

The preferred method of administration is parenterally by intravenous (i.v.) infusion. Alternatively, the compound may be administered intramuscularly (i.m.).

For adults, a dose of about 5 to about 50 mg of the formula I antibacterial compound per kg of body weight is administered from 1 to 6 times per day. The preferred dosage ranges from about 250 mg to about 1000 mg of the compound given one to four times per day.

More specifically, for mild infections a dose of 250 mg two to four times daily is preferred. For moderate infections against highly susceptible gram positive organisms a dose of 500 mg b.i.d. to q.i.d. is preferred. For severe, life-threatening infections against organisms at the upper limits of sensitivity to the antibiotic, a dose of about 1000–2000 mg two to six times daily is preferred.

For children, a dose of 5–25 mg/kg of body weight given 1 to 4 times per day is preferred; a dose of 10 mg/kg b.i.d., t.i.d. or q.i.d. is recommended.

The invention is further described in connection with the following non-limiting examples.

EXAMPLE ONE

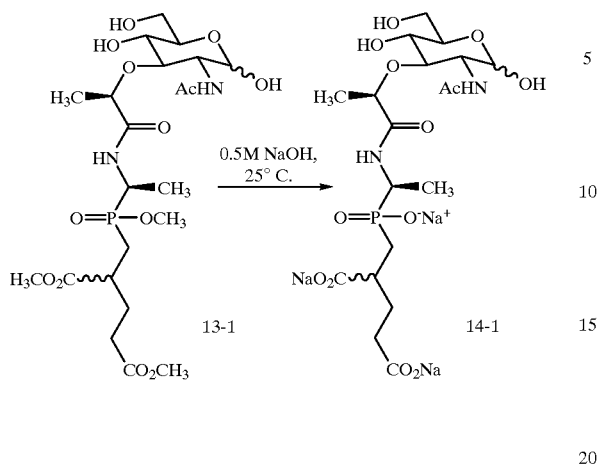

To a solution of triester 13-1 (0.039 g, 0.068 mmol) in 1.8 mL H$_2$O was added NaOH (0.2 mL of a 5N solution, 1 mmol). The reaction was allowed to stir 6 h at 25° C., at which time it was adjusted to pH 5.0 by the addition of AG50W-X8 (hydrogen form) ion exchange resin (Bio-Rad). The resin was filtered off and the solution was adjusted to pH 8.0 with 0.5 M NaOH. This solution was then applied to a column (10 mL) of Bio-Gel P2 Fine (Bio-Rad). Elution with H$_2$O afforded 0.036 g of compound 14-1 as the trisodium salt.

EXAMPLE TWO

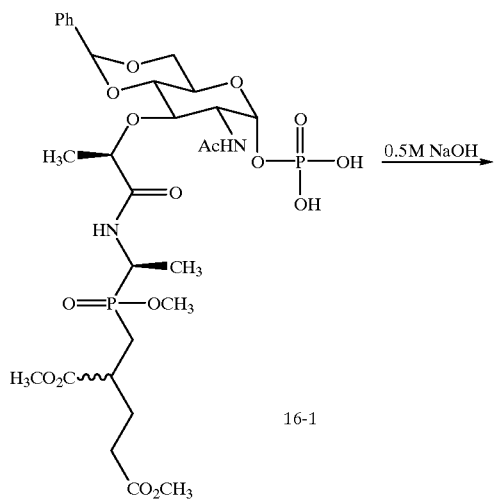

-continued

To a solution of triester 16-1 (0.010 g, 0.014 mmol) in 2 mL H$_2$O was added NaOH (0.2 mL of a 5N solution, 1 mmol). The reaction was allowed to stir 17 h at 25° C., at which time it was adjusted to pH 5.5 by the addition of AG50W-X8 (hydrogen form) ion exchange resin (Bio-Rad). The resin was filtered off and the solution was adjusted to pH 8.5 with 0.5 M NaOH. This solution was then applied to a column (5 mL) of Bio-Gel P2 Fine (Bio-Rad). Elution with H$_2$O afforded 0.009 g of compound 18-1 as the pentasodium salt.

EXAMPLE THREE

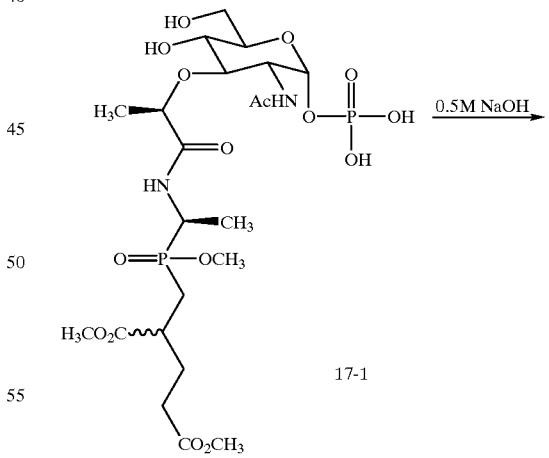

-continued

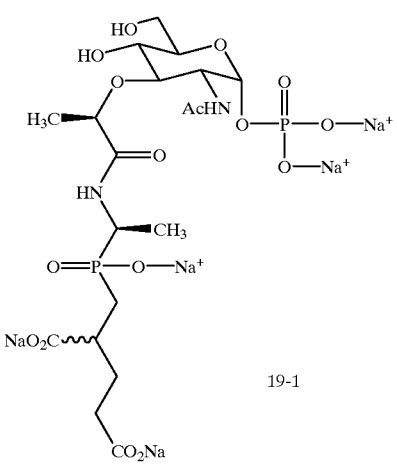

19-1

-continued

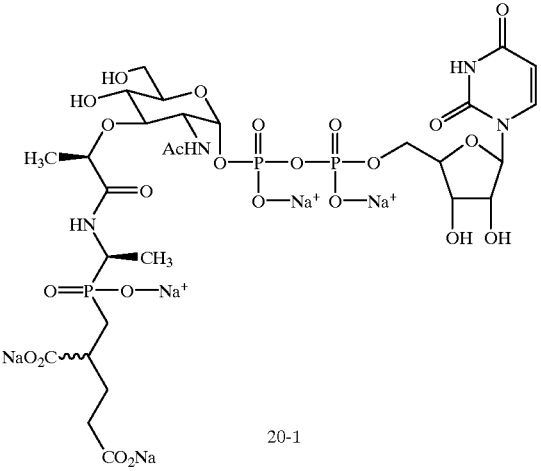

20-1

To a solution of triester 17-1 (0.015 g, 0.023 mmol) in 2.7 mL H$_2$O was added NaOH (0.3 mL of a 5N solution, 1.5 mmol). The reaction was allowed to stir 3.5 h at 25° C., at which time it was adjusted to pH 5.5 by the addition of AG50W-X8 (hydrogen form) ion exchange resin (Bio-Rad). The resin was filtered off and the solution was adjusted to pH 8.5 with 0.5 M NaOH. This solution was then applied to a column (5 mL) of Bio-Gel P2 Fine (Bio-Rad). Elution with H$_2$O afforded 0.011 g of compound 19-1 as the pentasodium salt.

EXAMPLE FOUR

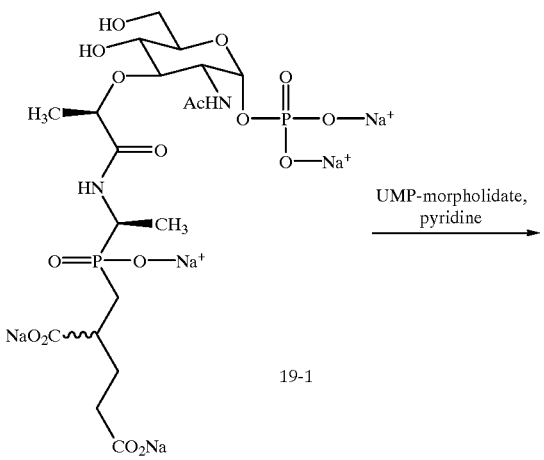

The pentasodium salt of 19-1 (0.010 g, 0.014 mmol) from Example Three was dissolved in 3 mL H$_2$O and the solution was adjusted to pH 4.0 with AG50W-X8 (hydrogen form) ion exchange resin (Bio-Rad). The resin was filtered off, 3 mL pyridine was added, and the solution was concentrated to dryness. The residue was azeotropically dried with anhydrous pyridine (5×1 mL). In a separate flask, uridine 5'-monophosphomorpholidate (0.014 g, 0.021 mmol, Sigma) was azeotropically dried with anhydrous pyridine (5×1 mL). The UMP-morpholidate was dissolved in 1 mL anhydrous pyridine and was added to the dried phosphate 19-1.

The mixture was concentrated to dryness and was redissolved in 0.5 mL anhydrous pyridine. The reaction was allowed to stir under N$_2$ at 37° C. for 3 days. The residue was chromatographed on preparative thin layer silica plates (7:3:1 isopropanol:H$_2$O:NH$_4$OH). The slowest-moving UV-active band was extracted from the silica with 4:1 isopropanol:H$_2$O. This material was applied to a column (15 mL) of Bio-Gel P2 Fine (Bio-Rad). Elution with H$_2$O afforded 0.001 g of 20-1.

Mur D enzymatic assay

The reaction catalyzed by MurD can be followed by the formation and HPLC separation of radiolabelled UDP-N-acetyl-muramyl-L-alanine-D-glutamate from radiolabelled D-glutamate. A typical reaction mixture contained the following, 100 mM Bis-Tris Propane, pH 8.0, 5 mM MgCl$_2$, 0.5 mM ATP, 25 µM D-glutamic acid, 25 µM UDP-N-acetylmuramyl-L-alanine, 119 nM D-[2,3,4-$^3$H] glutamic acid and 10% DMSO. The reaction was initiated by the addition of recombinant MurD. The reaction was incubated at room temperature for 20 minutes and quenched with 200 µl of 0.3 M KH$_2$PO$_4$, pH 3.5. The separation of radiolabelled reactant from radiolabelled product was accomplished via weak anion exchange HPLC using a HICHROM Synchropak AX300 column (25 cm×4.6 mm i.d.) attached to an IN/US β-Ram radioflow detector. Elution was with 0.15 M KH$_2$PO$_4$, pH 3.5, at 1.5 ml/minute isocratic with a run time of 20 minutes. Enzyme activity was linear for 20 minutes and reported as (% cpm (counts per minutes) D-[2,3,4-$^3$H]-UDP-N-acetyl-muramyl-L-alanine-D-glutamate)/(% cpm D-[2,3,4$^3$H]-glutamic acid). The HPLC system consists of two Shimadzu LC-10AD pumps, a Shimadzu SCL-10A gradient controller, a Shimadzu SIL-10A autosampler, and an IN/US β-Ram radioactivity flow monitor. Data were digitized and analyzed on Shimadzu Class-VP chromatographic software, equipped with MTP-PLUS.

The inhibition constants ($IC_{50}$) were determined by measuring the amount of radiolabelled UDP-N-acetyl-muramyl-L-alanine-D-glutamate formed after 20 minutes in the absence and presence of increasing concentrations of inhibitor. $IC_{50}$ values were determined graphically by plotting the inhibitor concentration versus the activity using Sigma Plot (Jandel Scientific). The values were calculated by fitting the data to y=1/(1+x/b), where x is the inhibitor concentration, y is the relative activity, and b is the $IC_{50}$ (Segel, 1975).

What is claimed is:

1. A compound represented by structural formula 1:

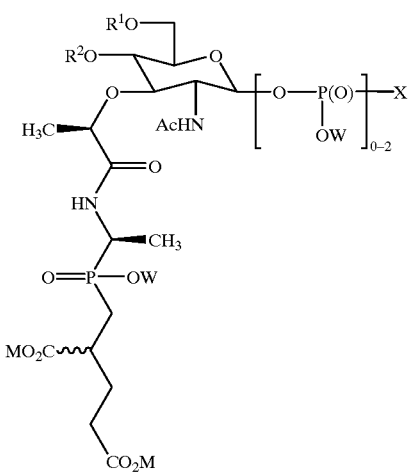

1 or a salt or hydrate thereof wherein:

X represents OH, $OC_{1-6}$ alkyl, O-aryl, O-Har, uridinyl, 5-iodouridinyl or O—Y$^+$, wherein Y$^{30}$ represents a charge balancing group;

$R^1$ and $R^2$ independently represent H or $C_{1-6}$ alkyl, or $R^1$ and $R^2$ taken together represent $C_{1-6}$ allylene unsubstituted or substituted with from 1–2 aryl or Har groups;

W represents H, aryl, $C_{1-6}$ alkyl or a charge balancing group;

and each M independently represents a member selected from the group consisting of: H, a charge balancing group and a protecting group.

2. A compound in accordance with claim 1 wherein X represents a member selected from the group consisting of: OH, O-aryl, O-Har, uridinyl, 5-iodouridinyl and O—Y$^+$, with Y$^+$ representing a charge balancing group.

3. A compound in accordance with claim 2 wherein X represents O$^-$ Y$^{30}$ and Y$^{30}$ represents a charge balancing group selected from the group consisting of: Na$^+$, K$^+$ and Ca$^{2+}$ (half molar equivalent).

4. A compound in accordance with claim 1 wherein $R^1$ and $R^2$ independently represent H or $C_{1-6}$ alkyl, or taken together represent $C_{1-6}$ alkylene substituted with 1–2 aryl groups.

5. A compound in accordance with claim 4 wherein $R^1$ and $R^2$ represent H or methyl.

6. A compound in accordance with claim 1 wherein W represents H, $C_{1-6}$ alkyl or a charge balancing group.

7. A compound in accordance with claim 6 wherein W represents H or a charge balancing group selected from the group consisting of: Na$^+$, K$^+$ and Ca$^{2+}$ (half molar equivalent).

8. A compound in accordance with claim 1 wherein each M independently represents H or a charge balancing group.

9. A compound in accordance with claim 8 wherein each M independently represents a charge balancing group selected from Na$^+$, K$^+$ and Ca$^{2+}$ (half molar equivalent).

10. A compound in accordance with claim 1 wherein each M independently represents a protecting group.

11. A compound in accordance with claim 10 wherein each M independently represents a protecting group selected from the group consisting of: $C_{1-6}$ alkyl, benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl) ethyl, phenacyl, p-methoxybenzyl, acetonyl, p-methoxyphenyl, 4-pyridylmethyl and t-butyl.

12. A compound in accordance with claim 11 wherein each M independently represents a protecting group selected from the group consisting of: $C_{1-6}$ alkyl, benzhydryl, PNB, allyl, Bn, TMS, TBDMS, acetonyl and p-methoxyphenyl.

13. A compound in accordance with claim 1 useful as an antibacterial agent represented by the formula:

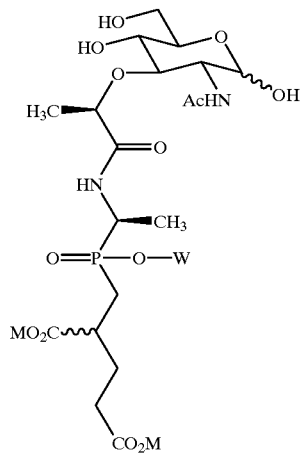

14-1

-continued
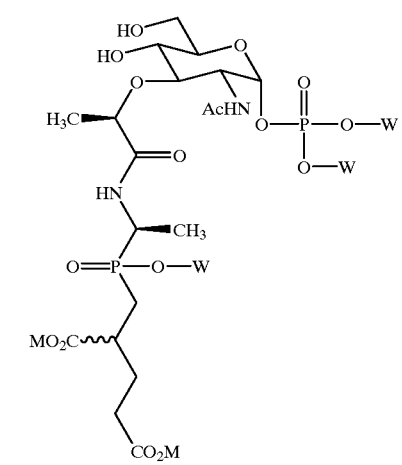
19-1
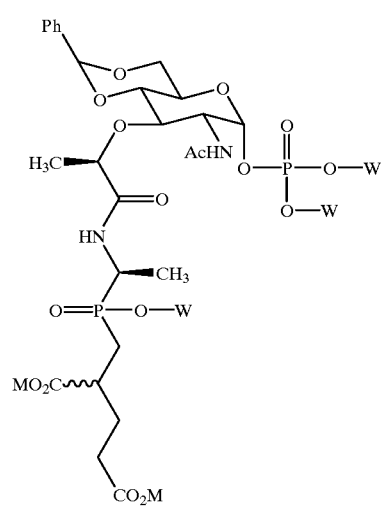
18-1
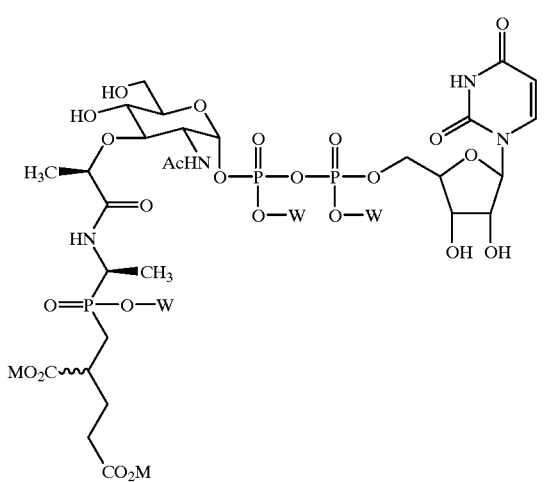
20-1
wherein M and W independently represent H or charge balancing groups.
14. A compound in accordance with claim 1 represented by the structural formula:
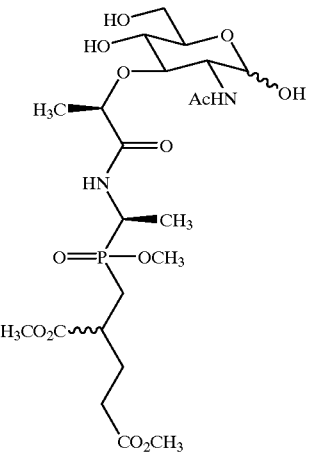
13-1
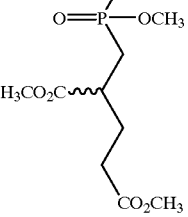
17-1
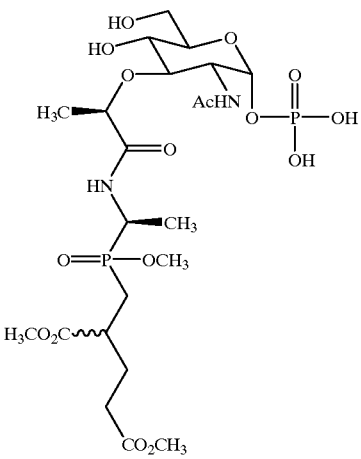
16-1
or a salt thereof.

15. A compound represented by formula 1-a:

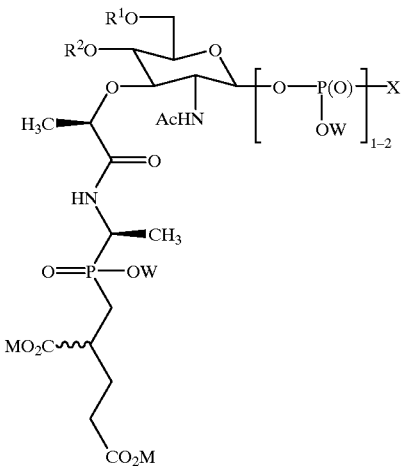

wherein:

X represents OH, O—aryl, O—Har, uridinyl, 5-iodouridinyl or O—Y$^+$, wherein Y$^{30}$ represents a charge balancing group selected from the group consisting of: Na$^+$, K$^+$ and Ca$^{2+}$ (half molar equivalent);

R$^1$ and R$^2$ independently represent H or C$_{1-6}$ alkyl, or R$^1$ and R$^2$ taken together represent C$_{1-6}$ alkylene substituted with from 1–2 aryl groups;

W represents H or a charge balancing group selected from the group consisting of: Na$^+$, K$^+$ and Ca$^{2+}$ (half molar equivalent);

and each M independently represents H or a charge balancing group selected from the group consisting of: Na$^+$, K$^+$ and Ca$^{2+}$ (half molar equivalent).

16. A pharmaceutical composition which is comprised of a compound in accordance with claim 1 in combination with a carrier.

17. A method of treating a bacterial infection in a mammalian patient in need of such treatment which is comprised of administering to said patient a compound in accordance with claim 1 in an amount which is effective for treating a bacterial infection.

* * * * *